US010136669B2

(12) United States Patent
Mine et al.

(10) Patent No.: US 10,136,669 B2
(45) Date of Patent: Nov. 27, 2018

(54) METHOD FOR DECREASING VISCERAL FAT OR INCREASING ENERGY CONSUMPTION

(71) Applicant: AJINOMOTO CO., INC., Tokyo (JP)

(72) Inventors: Tomoyuki Mine, Kanagawa (JP); Naoki Hayashi, Kanagawa (JP); Itaru Kon, Kanagawa (JP); Kazunori Saima, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 166 days.

(21) Appl. No.: 15/247,070

(22) Filed: Aug. 25, 2016

(65) Prior Publication Data

US 2016/0374381 A1 Dec. 29, 2016

Related U.S. Application Data

(60) Division of application No. 14/051,576, filed on Oct. 11, 2013, now abandoned, which is a continuation of application No. PCT/JP2012/060186, filed on Apr. 13, 2012.

(30) Foreign Application Priority Data

Apr. 13, 2011 (JP) .................................. 2011-089626

(51) Int. Cl.
A23L 33/12 (2016.01)
A61K 31/07 (2006.01)
A61K 31/198 (2006.01)
A61K 31/20 (2006.01)
A61K 31/202 (2006.01)
A61K 31/355 (2006.01)
A61K 31/375 (2006.01)
A61K 31/4415 (2006.01)
A61K 31/51 (2006.01)
A61K 31/525 (2006.01)
A61K 31/714 (2006.01)
A61K 33/04 (2006.01)
A61K 33/30 (2006.01)
A61K 38/05 (2006.01)
A23L 2/52 (2006.01)
A23L 33/115 (2016.01)
A23L 33/15 (2016.01)
A23L 33/155 (2016.01)
A23L 33/17 (2016.01)
A23L 33/175 (2016.01)
A23L 33/18 (2016.01)

(52) U.S. Cl.
CPC ................ *A23L 33/12* (2016.08); *A23L 2/52* (2013.01); *A23L 33/115* (2016.08); *A23L 33/15* (2016.08); *A23L 33/155* (2016.08); *A23L 33/17* (2016.08); *A23L 33/175* (2016.08); *A23L 33/18* (2016.08); *A61K 31/07* (2013.01); *A61K 31/198* (2013.01); *A61K 31/20* (2013.01); *A61K 31/202* (2013.01); *A61K 31/355* (2013.01); *A61K 31/375* (2013.01); *A61K 31/4415* (2013.01); *A61K 31/51* (2013.01); *A61K 31/525* (2013.01); *A61K 31/714* (2013.01); *A61K 33/04* (2013.01); *A61K 33/30* (2013.01); *A61K 38/05* (2013.01); *A23V 2002/00* (2013.01)

(58) Field of Classification Search
CPC .......... A23L 33/12; A23L 33/17; A23L 33/18; A23L 33/175; A23L 33/115; A23L 33/15; A23L 33/155; A23L 2/52; A61K 31/07; A61K 31/198; A61K 31/20; A61K 31/202; A61K 31/355; A61K 31/375; A61K 31/4415; A61K 31/51; A61K 31/525; A61K 31/714; A61K 33/04; A61K 33/30; A61K 38/05; A23V 2002/00
See application file for complete search history.

(56) References Cited

U.S. PATENT DOCUMENTS

| 6,077,828 | A | 6/2000 | Abbruzzese et al. |
| 2004/0097404 | A1 | 5/2004 | Kessler et al. |
| 2004/0142018 | A1 | 7/2004 | Takeuchi et al. |
| 2005/0032898 | A1 | 2/2005 | Ohtani |
| 2008/0003335 | A1 | 1/2008 | Singh et al. |
| 2008/0275120 | A1* | 11/2008 | Peters ..................... A61K 35/20 514/561 |
| 2009/0111877 | A1 | 4/2009 | Yamka et al. |
| 2009/0203606 | A1 | 8/2009 | Wolfe et al. |
| 2010/0104599 | A1 | 4/2010 | Yamka et al. |
| 2010/0137404 | A1* | 6/2010 | Yamka ................... A23K 50/40 514/44 A |
| 2010/0143497 | A1 | 6/2010 | Yamka et al. |
| 2010/0189816 | A1 | 7/2010 | Schneid |
| 2011/0059202 | A1 | 3/2011 | Zicker et al. |
| 2014/0044828 | A1 | 2/2014 | Mine et al. |

FOREIGN PATENT DOCUMENTS

| CN | 101325951 | 12/2008 |
| CN | 101662951 | 3/2010 |

(Continued)

OTHER PUBLICATIONS

Matsuda, N. et al., The Japanese Journal of Clinical Nutrition (Aug. 2013), pp. 38-43.

(Continued)

Primary Examiner — Anthony J Weier
(74) Attorney, Agent, or Firm — Cermak Nakajima & McGowan LLP; Shelly Guest Cermak

(57) ABSTRACT

A nutritional composition is provided which has an effective prophylactic and/or improving effect for various symptoms of muscle mass decrease, decreased basal metabolism, low body temperature, suppression of obesity, suppression of visceral fat accumulation, hyperglycemia, hyperlipidemia and the like in elderly people. The nutritional composition can include n-3 fatty acid and one or more of free lysine, dipeptides containing lysine, and lysine salts, wherein the content of free lysine, dipeptides containing lysine, and/or lysine salts is 0.1 g-10.0 g per 100 kcal of the composition, and the content of the total amount of n-3 fatty acid is 0.17 g-5.00 g per 100 kcal of the composition.

2 Claims, 3 Drawing Sheets
Specification includes a Sequence Listing.

(56) References Cited

FOREIGN PATENT DOCUMENTS

| | | |
|---|---|---|
| CN | 101686712 | 3/2010 |
| CN | 108801219 | 8/2010 |
| EP | 0265099 | 4/1988 |
| EP | 1774973 | 4/2007 |
| EP | 2374452 | 10/2011 |
| JP | 64-20060 | 1/1989 |
| JP | 11-508282 | 7/1999 |
| JP | 2004-513912 | 5/2004 |
| JP | 2006-304792 | 11/2006 |
| JP | 2008-539793 | 11/2008 |
| JP | 2009-511576 | 3/2009 |
| JP | 2009-102235 | 5/2009 |
| JP | 2010-105946 | 5/2010 |
| JP | 2010-518865 | 6/2010 |
| WO | WO97/39749 | 10/1997 |
| WO | WO02/15720 | 2/2002 |
| WO | WO2004/026294 | 4/2004 |
| WO | WO2006/105112 | 10/2006 |
| WO | WO2006/127424 | 11/2006 |
| WO | WO2007/043870 | 4/2007 |
| WO | WO2008/018043 | 2/2008 |
| WO | WO2008/046870 | 4/2008 |
| WO | WO2008/103958 | 8/2008 |
| WO | WO2009/015879 | 2/2009 |
| WO | WO2009/088738 | 7/2009 |
| WO | WO2009/100241 | 8/2009 |
| WO | WO2010/002257 | 1/2010 |
| WO | WO2010/064714 | 6/2010 |
| WO | WO2011/021926 | 2/2011 |

OTHER PUBLICATIONS

Volpi, E., et al., "Essential amino acids are primarily responsible for the amino acid stimulation of muscle protein anabolism in healthy elderly adults," Am. J. Clin. Nutr. 2003;78:250-258.
Smith, H. J., et al., "Effect of eicosapentaenoic acid, protein and amino acids on protein synthesis and degradation in skeletal muscle of cachectic mice," Br. J. Cancer 2004;91:408-412.
Argilés, J. M., et al., "Therapeutic Strategies in Cachexia: Current and Future Directions," Drugs of the Future 2010;35(1):41-52.
Lombardo, Y. B., et al., "Effects of dietary polyunsaturated n-3 fatty acids on dyslipidemia and insulin resistance in rodents and humans. A review," J. Nutr. Biochem. 2006;17;1-13.
Jump, D. B, et al., "Fatty Acid Regulation of Hepatic Gene Transcription," J. Nutr. 2005;135(11):2503-2506.
Van Norren, K., et al., "Dietary supplementation with a specific combination of high protein, leucine, and fish oil improves muscle function and daily activity in tumour-bearing cachectic mice," Br. J. Cancer 2009;100:713-722.
Faber, J., et al., "Beneficial immune modulatory effects of a specific nutritional combination in a murine model for cancer cachexia," Br. J. Cancer 2008;99:2029-2036.
Gingras, A.-A., et al., "Long-chain omega-3 fatty acids regulate bovine whole-body protein metabolism by promoting muscle insulin signalling to the Akt-mTOR-S6K1 pathway and insulin sensitivity," J. Physiol. 2007;579.1:269-284.
Lorite, M. J., et al., "Induction of muscle protein degradation by a tumour factor," Br. J. Cancer 1997;76(8):1035-1040.
Ling, P. R., et al., "Structured lipid made from fish oil and medium-chain triglycerides alters tumor and host metabolism in Yoshida-sarcoma-bearing rats," Am. J. Clin. Nutr. 1991;53:1177-1184.
Gollaher, C. J., et al., "The Effect of Increasing Levels of Fish Oil-Containing Structured Triglycerides on Protein Metabolism in Parenterally Fed Rats Stressed by Burn Plus Endotoxin," Journal of Parenteral and Enteral Nutrition 1993;17(3):247-253.
Teo, T. C., et al., "Administration of Structured Lipid Composed of MCT and Fish Oil Reduces Net Protein Catabolism in Enterally Fed Burned Rats," Annals of Surgery 1989;210(1):100-10.
Coëffier, M., et al., "Quelle pharmaconutrition pour lutter contre la sarcopénie?" Nutrition Clinique et Metabolisme 2009;23(2):76-79, with English abstract thereof.
Cave, M.C., et al., "Obesity, Inflammation, and the Potential Application of Pharmaconutrition," Nutrition in Clinical Practice 2008;23(1):16-34.
Bloomer, R. J., "The Role of Nutritional Supplements in the Prevention and Treatment of Resistance Exercise-Induced Skeletal Muscle Injury," Sports Med. 2007;37(6):519-532.
Siddiqui, R., et al., "Nutrition Modulation of Cachexia/Proteolysis," Nutrition in Clinical Practice 2006;21(2):155-167.
Chan, D. C., et al., "Randomized controlled trial of the effect of n-3 fatty acid supplementation on the metabolism of apolipoprotein B-100 and chylomicron remnants in men with visceral obesity," Am. J. Clin. Nutr. 2003;77:300-307.
International Search Report for PCT Patent App. No. PCT/JP2012/060186 (dated Jun. 26, 2012).
Office Action from Chinese Patent App. No. 201280017843.1 (dated Dec. 31, 2014) with English language translation thereof.
Smith, G. I., et al., "Dietary omega-3 fatty acid supplementation increases the rate of muscle protein synthesis in older adults: a randomized controlled trial," Am. J. Clin. Nutr. 2011;93:402-412.
Supplementary European Search Report for European Patent App. No. 12771356.8 (dated Mar. 4, 2015).
Derwent Abstract for CN101801219 published Aug. 11, 2010.
Derwent Abstract for CN101662951 published Mar. 3, 2010.
Second Office Action from Chinese Patent App. No. 201280017843.1 (dated Oct. 14, 2015) with English language translation thereof.
Notice of Reasons for Refusal for Japanese Patent App. No. 2013-509995 (dated Nov. 4, 2015) with English language translation thereof.
Japanese Journal of Medicine and Pharmaceutical Science, 2008, vol. 59, No. 5, pp. 743-750. (A concise explanation of this reference is provided in the Notice of Reasons for Refusal for Japanese Patent App. No. 2013-509995).
Yoshihara, D., et al., "Effect of Coexistence of Di-, Tripeptides and Amino Acids on Absorption of Nitrogen Source," Journal of Japanese Society of Nutrition and Food Science, 1997, vol. 50, No. 6, pp. 411-416, with English abstract.
Notice of Reasons for Refusal for Japanese Patent App. No. 2013-509995 (dated Apr. 12, 2016) with English translation thereof.

* cited by examiner

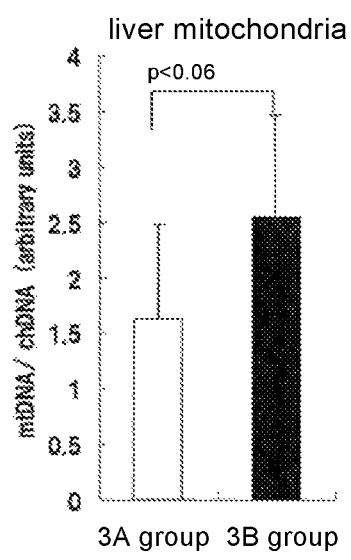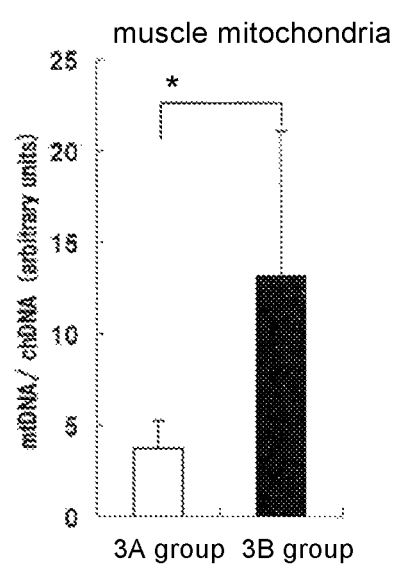
Fig. 4A                    Fig. 4B

```
                       SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
acacgccata atggcactgg                                          20

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
cagtcttggc agtgcagat                                           19

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
cgcaaaaccc aatcacctaa                                          20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttggggtttg gcattaagag                                          20
```

METHOD FOR DECREASING VISCERAL FAT OR INCREASING ENERGY CONSUMPTION

This application is a Divisional of, and claims priority under 35 U.S.C. § 120 to, U.S. patent application Ser. No. 14/051,576, filed Oct. 11, 2013, now abandoned, which as a Continuation of, and claimed priority under 35 U.S.C. § 120 to, International Application No. PCT/JP2012/060186, filed Apr. 13, 2012, and claimed priority therethrough under 35 U.S.C. § 119 to Japanese Patent Application No. 2011-089626, filed Apr. 13, 2011, the entireties of which are incorporated by reference herein. Also, the Sequence Listing filed electronically herewith is hereby incorporated by reference (File name: 2016-08-25T_US-504D_Seq_List; File size: 1 KB; Date recorded: Aug. 25, 2016).

FIELD OF THE INVENTION

The present invention relates to a nutritional composition containing particular amounts of a particular amino acid and n-3 fatty acid, which is effective for increasing muscle mass and/or suppressing a decrease in the muscle mass. More particularly, the present invention relates to a nutritional composition containing particular amounts of one or more of the following: free lysine, dipeptides containing lysine and lysine salts, and n-3 fatty acid, which is effective for increasing muscle mass and/or suppressing a decrease in the muscle mass.

BRIEF DESCRIPTION OF THE RELATED ART

In elderly people, a specific skeletal muscle decrease called sarcopenia can occur. A decrease in skeletal muscle reduces the amount of activity elderly people are able to do, and the decreased amount of activity can cause further loss of muscle strength, thus forming a vicious circle. A decrease in the amount of activity also can decrease the basal energy metabolism. This condition is particularly apparent when in a bedridden state.

Moreover, elderly people have a high risk of falling when undernourished. According to a search of the Social Insurance Institute in Japan, about 40% of hospital patients and about 30% of home-care patients are undernourished. Even when energy ingestion is increased in an attempt to improve the nutrient condition, muscle mass cannot be recovered. Conversely, fat accumulates and leads to metabolism-associated diseases such as insulin resistance, diabetes, hyperlipidemia, and osteoporosis (Clinical Nutrition, 2008, 8: 38-43).

To counter muscle mass decrease, protein ingestion is recommended. In fact, it has been reported that ingestion of 18 g of an essential amino acid mixture increased protein synthesis of the skeletal muscle (Am J Clin Nutr, 2003, 78: 250-258). However, ingesting a large amount of amino acids, such as up to 18 g, all at once not only is difficult for elderly people due to their depressed kidney function due to aging, but also is risky since it may over burden on the kidneys. To increase the muscle mass in elderly people, therefore, not only supplementing with a general protein supplementation, but also ingestion of a more efficient composition is necessary.

Ingestion of lysine is known to increase growth and muscle mass in community residents and animals living on corn and wheat (JP-A-2008-539793). However, this is because the protein composition of the staple food is not balanced and lysine becomes a limiting amino acid. In most areas where protein is not necessarily obtained largely from corn and wheat, ingestion of lysine alone does not show a clear effect on the growth of the whole body, or an increase in the muscle mass that appears as one manifestation thereof.

JP-A-H11-508282 discloses a composition for patients with cachexia and/or anorexia, which contains a mixed oil with a weight ratio of n-6 fatty acid to n-3 fatty acid of 0.1-3.0, amino acid containing branched chain amino acid, and antioxidant such as β-carotene, vitamin C, vitamin E, and selenium. In addition, Br J Cancer, 2004, 91: 408-412 reports that a carcinoma cachexia model mouse ingested with n-3 fatty acid and a high leucine-containing protein diet shows a decrease in the body weight and an increase in the muscle mass. In the target patients, particular cytokines (TNF-α, IL-6 and the like) due to cachexia in the late stages of cancer are involved, and the muscle protein secretion decrease occurs based on the cytokines. It is assumed that n-3 fatty acid suppresses secretion of the cytokines, and branched chain amino acid such as leucine aids muscle protein synthesis, whereby the decrease of muscle proteins can be prevented. In other words, this composition was studied for treating carcinoma cachexia wherein cytokine-dominant protein decrease was extreme. However, this decrease is vastly different from the muscle mass decrease in general elderly people experience due to a decreased amount of activity by being bedridden and the like, and the effect is unknown.

Although n-3 fatty acid is used as a hypertriglyceridemia improving agent, a single use of n-3 fatty acid has been reported to show no effect on the weight increase of muscle (Drugs of the Future, 2010, 35: 41-52 and J Nutr Biochem, 2006, 17: 1-13).

While n-3 fatty acid has been reported to increase mRNA expression of an enzyme involved in fat oxidation (J Nutr, 2005, 135: 2503-2508), enhanced energy metabolism causing enhanced synthesis of protein such as muscle has not been confirmed to date.

As mentioned above, as the situation stands, a nutritional composition having an appropriate amino acid ratio, containing n-3 fatty acid, and having a function to maintain or increase the muscle mass of elderly people has not been provided heretofore.

SUMMARY OF THE INVENTION

A novel nutritional composition is described having a preventive and/or improving effect on a decrease in the muscle mass, particularly said effect for elderly people with a decreased muscle mass due to a decreased amount of activity.

A composition is described that contains particular amount(s) of one or more kinds of free lysine, dipeptides containing lysine and lysine salts, and a particular amount of n-3 fatty acid that can prevent and/or improve a decrease in the muscle mass, can improve hyperglycemia and hyperlipidemia by suppressing obesity and suppressing accumulation of visceral fat, and such effect is remarkable particularly in elderly people.

It is an aspect of the present invention to provide a nutritional composition comprising n-3 fatty acid and an ingredient selected from the group consisting of free lysine, dipeptides containing lysine, lysine salts, and combinations thereof; wherein the ingredient is present in the composition in an amount of 0.1 g-10.0 g per 100 kcal of the composition, and wherein the n-3 fatty acid is present in the composition in an amount of 0.17 g-5.00 g per 100 kcal of the composition.

It is a further aspect of the present invention to provide the nutritional composition as described above, further comprising a branched chain amino acid selected from the group consisting of valine, leucine, and isoleucine.

It is a further aspect of the present invention to provide the nutritional composition as described above, wherein the branched chain amino acid is present in the composition in an amount of 1.0 g-20 g per 100 kcal of the composition.

It is a further aspect of the present invention to provide the nutritional composition as described above, wherein the branched chain amino acid in a free form is present in the composition in an amount of 0.1 g-15 g per 100 kcal of the composition.

It is a further aspect of the present invention to provide the nutritional composition as described above, wherein the n-3 fatty acid is selected from the group consisting of eicosapentaenoic acid, docosapentaenoic acid, docosahexaenoic acid, and combinations thereof.

It is a further aspect of the present invention to provide the nutritional composition as described above, comprising 10 mg-3000 mg of eicosapentaenoic acid per 100 kcal of the composition.

It is a further aspect of the present invention to provide the nutritional composition as described above, further comprising a vitamin selected from the group consisting of:
  0.2 mg-20.0 mg of vitamin B1 per 100 kcal of the composition,
  0.25 mg-20.0 mg of vitamin B2 per 100 kcal of the composition,
  0.3 mg-20.0 mg of vitamin B6 per 100 kcal of the composition,
  0.3 µg-20.0 µg of vitamin B12 per 100 kcal of the composition, and
  combinations thereof.

It is a further aspect of the present invention to provide the nutritional composition as described above, further comprising a vitamin selected from the group consisting of:
  50 µg retinol equivalents-2500 µg retinol equivalents of vitamin A per 100 kcal of the composition,
  10 mg-700 mg of vitamin C per 100 kcal of the composition,
  1 mg-50 mg of vitamin E based on α-tocopherol per 100 kcal of the composition, and
  combinations thereof.

It is a further aspect of the present invention to provide the nutritional composition as described above, comprising 1 mg-50 mg of zinc per 100 kcal of the composition and/or 1.0 µg-50.0 µg of selenium per 100 kcal of the composition.

It is a further aspect of the present invention to provide the nutritional composition as described above, comprising medium chain fatty acid oil in an amount of 10 wt %-65 wt % relative to the total amount of lipid.

It is a further aspect of the present invention to provide the nutritional composition as described above, which is capable of increasing muscle mass and/or suppressing a decrease in the muscle mass.

It is a further aspect of the present invention to provide the nutritional composition as described above, which is capable of decreasing visceral fat or increasing energy consumption.

It is a further aspect of the present invention to provide the nutritional composition as described above, which is capable of an effect selected from the group consisting of prophylaxis and/or improvement of muscle weakness symptom, promotion of rehabilitation effect for muscle recovery, prophylaxis and/or improvement of dyslipidemia associated with visceral fat increase, prophylaxis and/or improvement of hyperglycemia associated with visceral fat increase, prophylaxis and/or improvement of fatty liver associated with visceral fat increase, prophylaxis and/or improvement of deteriorated liver function associated with visceral fat increase, prophylaxis and/or improvement of decrease in basal energy consumption, prophylaxis and/or improvement of decrease in basal body temperature, prophylaxis and/or improvement of muscle mass decrease unaccompanied by an increase in inflammatory cytokine, improvement of low nutrient condition, improvement of deterioration in locomotorium, prophylaxis and/or improvement of locomotive syndrome, prevention of falling, increase of muscle mass in sports, and combinations thereof.

It is a further aspect of the present invention to provide a method for increasing muscle mass and/or suppressing a decrease in muscle mass, comprising administering an effective amount of the composition as described above.

It is a further aspect of the present invention to provide a method for decreasing visceral fat or increasing energy consumption, comprising administering an effective amount of the composition as described above.

It is a further aspect of the present invention to provide a method for treating a condition comprising administering an effective amount of the composition as described above, wherein said condition is selected from the group consisting of prophylaxis and/or improvement of muscle weakness symptom, a method for the promotion of rehabilitation effect for muscle recovery, a method for the prophylaxis and/or improvement of dyslipidemia associated with visceral fat increase, a method for the prophylaxis and/or improvement of hyperglycemia associated with visceral fat increase, a method for the prophylaxis and/or improvement of fatty liver associated with visceral fat increase, a method for the prophylaxis and/or improvement of deteriorated liver function associated with visceral fat increase, a method for the prophylaxis and/or improvement of decrease of basal energy consumption, a method for the prophylaxis and/or improvement of decrease of basal body temperature, a method for the prophylaxis and/or improvement of muscle mass decrease unaccompanied by an increase in inflammatory cytokine, a method for the improvement of low nutrient condition, a method for the improvement of deterioration in locomotorium, a method for the prophylaxis and/or improvement of locomotive syndrome, a method for prevention of falling, a method for increasing muscle mass in sports, and combinations thereof.

A method for producing an agent for increasing muscle mass and/or suppressing a decrease in muscle mass comprising formulating a composition as described above.

It is a further aspect of the present invention to provide a method for producing an agent for decreasing visceral fat or increasing energy consumption comprising formulating a composition as described above.

It is a further aspect of the present invention to provide a method for producing an agent for treating a condition comprising formulating a composition as described above, wherein the condition is selected from the group consisting of: the prophylaxis and/or improvement of muscle weakness symptom, promoting of rehabilitation effect for muscle recovery, the prophylaxis and/or improvement of dyslipidemia associated with visceral fat increase, the prophylaxis and/or improvement of hyperglycemia associated with visceral fat increase, the prophylaxis and/or improvement of fatty liver associated with visceral fat increase, the prophylaxis and/or improvement of deteriorated liver function associated with visceral fat increase, the prophylaxis and/or improvement of decrease of basal energy consumption, the prophylaxis and/or improvement of decrease of basal body temperature, the prophylaxis and/or improvement of muscle mass decrease unaccompanied by an increase in inflammatory cytokine, improvement of low nutrient condition, improving deterioration in locomotorium, the prophylaxis and/or improvement of locomotive syndrome, prevention of falling, increasing muscle mass in sports, and combinations thereof.

The nutritional composition as described herein is effective for increasing muscle mass and/or suppressing a decrease in muscle mass. In addition, the nutritional composition is effective for increasing energy consumption. In addition, the nutritional composition is particularly useful for decreasing visceral fat based on the effect of increasing energy consumption by enhanced fat utilization and the like. In addition, it is useful for the prophylaxis and/or improvement of dyslipidemia, hyperglycemia, fatty liver, and deterioration of liver function associated with visceral fat increase. Furthermore, by increasing muscle mass or suppressing a decrease in muscle mass by fat energy supply and the like, the nutritional composition is also useful for the prophylaxis and/or improvement of sarcopenia, chronic obstructive pulmonary disease (COPD), promotion of rehabilitation effect for muscle recovery, improvement of low nutrient condition, improvement of deterioration in locomotorium, prophylaxis and/or improvement of locomotive syndrome, prevention of falling, increasing muscle mass in sports and the like. Moreover, the nutritional composition is effective for the prophylaxis and/or improvement of a decrease in basal energy consumption, and prophylaxis and/or improvement of a decrease in basal body temperature. Furthermore, the nutritional composition is highly safe, and can be used for a long time without causing an excessive protein load even for elderly people with attenuated kidney function.

BRIEF DESCRIPTION OF THE DRAWINGS

FIGS. 4A and 4B shows a ratio of DNA amount of mitochondria gene (mtDNA) to that of nuclear coding gene (chDNA) of the groups as outlined in Experimental Example 3.

DESCRIPTION OF THE PREFERRED EMBODIMENTS

Figures 1A, 1B:
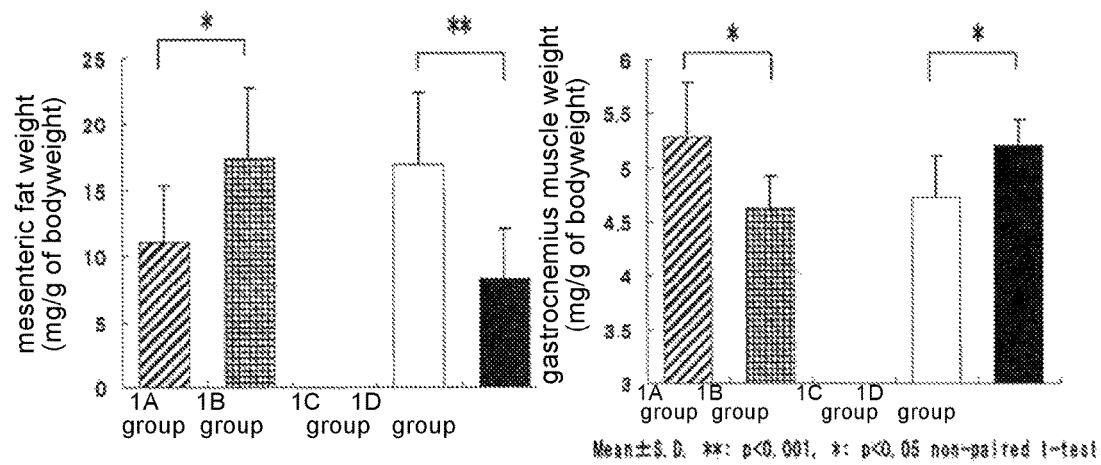
FIGS. 1A and 1B shows mesenteric fat weight and gastrocnemius muscle weight respectively, of the groups as outlined in Experimental Example 1.

The nutritional composition can include one or more of free lysine, dipeptides containing lysine, and/or lysine salts in a total amount of 0.1 g-10.0 g per 100 kcal of the composition, and n-3 fatty acid in a total amount of 0.17 g-5.00 g per 100 kcal of the composition.

Lysine is one of the essential amino acids, and is the limiting amino acid when corn, wheat, and the like are staple foods, and is particularly effectively when added to the feed for domestic animals, since it contributes to the efficient growth of the animal. In addition, lysine may be in any form as long as it is in a free form, dipeptide form, salt form, or the like (hereinafter the "lysine" can mean a concept encompassing free lysine, dipeptides containing lysine, lysine salts and the like). Since the lysine in the nutritional composition is in a free form, a dipeptide form, a salt form or the like, the composition can be used for a long time without causing an excessive protein load, even for elderly people with attenuated kidney function. While the lysine may be in the L form, D form, or DL form, the L form is a particular example. The lysine in various forms can be used alone, or two or more forms of lysine can be used in combination. While the form of lysine is not limited, examples of the lysine salts include acid addition salt, salt with base and the like. Examples of the acid to be added to lysine to form a salt include inorganic acids such as hydrogen chloride, hydrogen bromide, sulfuric acid, phosphoric acid; organic acids such as acetic acid, lactic acid, citric acid, tartaric acid, maleic acid, fumaric acid, monomethylsulfuric acid; acidic amino acids such as glutamate, aspartic acid, and the like. In addition, examples of the base that forms a salt with lysine include hydroxide or carbohydroxide of metal such as sodium, potassium, calcium, inorganic bases such as ammonia; organic bases such as ethylenediamine, propylenediamine, ethanolamine, monoalkylethanolamine, dialkylethanolamine, diethanolamine, and triethanolamine. More specific examples of the lysine salts include lysine hydrochloride, lysine acetate, lysine glutamate, lysine aspartate and the like. "Dipeptide" refers to an amino acid dimer wherein two amino acid molecules are peptide-bonded, and the "dipeptides containing lysine" can refer to a dipeptide wherein at least one molecule, or 2 molecules, of the dipeptide is lysine. Examples of the dipeptides containing lysine include lysyllysine and the like. Among these lysines, lysine in a salt form can be used, and L-lysine hydrochloride, L-lysine acetate, and L-lysine glutamate are particular examples when used in food. Moreover, since flavor, pH upon dissolution, and the like can vary depending on the form, the form of lysine can be appropriately changed depending on the use.

The amount of lysine can be 0.1 g-10.0 g per 100 kcal of the composition and, from the aspect of amino acid nutrition balance, can be 0.2-5.0 g, or 0.25-4.5 g. When the amount of lysine is less than 0.1 g per 100 kcal of the composition, the desired effect cannot be expected since the lysine is consumed making body protein or an energy source. Conversely, when the amount exceeds 10.0 g, a large amount of a single amino acid is ingested, which is not very desirable for the amino acid balance. The amount of lysine can be based on the free form.

While the daily intake of lysine is individually determined depending on the age, sex, body weight, diet condition, and the like, it can be 20 mg-400 mg, or 40 mg-200 mg, per kg human body weight, from the aspect of amino acid nutrition balance. While the maximum tolerable intake of lysine per day has not been clarified, when it is more than 20 g per human kg body weight, a large amount of a single amino acid is ingested, which is not very desirable for the amino acid balance.

The n-3 fatty acid can be an unsaturated fatty acid having a double bond at the third position from the methyl group end of the hydrocarbon chain. Examples thereof include eicosapentaenoic acid, docosahexaenoic acid, α-linolenic acid, docosapentaenoic acid, and the like. These may be used alone, or two or more kinds thereof may be used in combination.

The n-3 fatty acid is abundantly present in fats and oils such as fish oil, Japanese basil oil, and flaxseed oil. The n-3 fatty acids can be extracted from these fats and oils and used after purification. It is also possible to use n-3 fatty acids produced by a chemical synthesis method, a fermentation method and the like, and a commercially available product for food can also be used. As a lipid source, moreover, the fats and oils that contain an abundant amount of n-3 fatty acid can also be used directly.

The total amount of n-3 fatty acid present in the composition can be 0.17 g-5.00 g, 0.18 g-4.00 g, or 0.19 g-3.00 g, per 100 kcal of the composition. When the total amount is less than 0.17 g per 100 kcal of the composition, a clear effect cannot be expected. Conversely, an amount exceeding 5.00 g in total per 100 kcal of the composition is not very preferable in view of the flavor. In Japan, ingesting not less than 2 g of n-3 fatty acid per day is recommended. Fats and oils containing n-3 fatty acid may be directly used, or n-3 fatty acid or fats and oils that contain an abundant amount of n-3 fatty acids may be mixed with other oils and used, as long as the amount of the n-3 fatty acid falls within the aforementioned range.

The n-3 fatty acid can contain eicosapentaenoic acid, docosapentaenoic acid, and/or docosahexaenoic acid. When the n-3 fatty acid contains eicosapentaenoic acid, the amount of eicosapentaenoic acid can be 10 mg-3000 mg, 20 mg-2000 mg, 50 mg-1000 mg, per 100 kcal of the composition. In addition, the amount of eicosapentaenoic acid relative to the total amount of n-3 fatty acid can be 1 wt %-60 wt %, or 5 wt %-40 wt %. In Japan, ingesting not less than 1 g of eicosapentaenoic acid together with docosahexaenoic acid per day is recommended, and the upper limit is not particularly set.

The nutritional composition can further contain a total amount of 1.0 g-20 g of one or more kinds of branched chain amino acids, such as valine, leucine and/or isoleucine, per 100 kcal of the composition.

The branched chain amino acid can be valine, leucine, and/or isoleucine. The form of these branched chain amino acids is not particularly limited and may be any form such as a protein form, a peptide form, a salt form, or a free form. In consideration of the burden on the kidney and in an attempt to not increase the overall amount of protein, the free form is usually the most preferable. In this case, the L form, D form, or DL form can be used. In addition, as the aforementioned branched chain amino acid, any of the amino acids obtained by extraction from animals and plants etc., and purification thereof, and the amino acids obtained by a chemical synthesis method, a fermentation method, or a gene recombination method, may be used.

The above-mentioned branched chain amino acids have been found to be more highly effective when present in not less than about 0.1 g in total per 100 kcal of the composition, and an increased amount of the branched chain amino acid can be used when a stronger effect is expected. In consideration of degradation of the taste, the amount thereof per 100 kcal of the composition can be 1.0 g-20 g, or 1.2 g-12 g, in total. When the total amount of the branched chain amino acids excesses 20 g per 100 kcal of the composition, a large amount of a particular amino acid is ingested, which is not very preferable for the amino acid balance.

The branched chain amino acid may be in any form such as a free form, a peptide form, a protein form, or salt form. The branched chain amino acids may be all one type of form, or may be a mixture of two or more kinds of different forms. For example, the branched chain amino acid may consist solely of a branched chain amino acid in a free form, or may contain a branched chain amino acid in a free form and a branched chain amino acid in a protein form, and the like. When the nutritional composition contains a branched chain amino acid in a free form, the total amount thereof can be 0.1 g-15 g, or 0.25-12 g, per 100 kcal of the composition.

The amount of branched chain amino acid is typically expressed based on the free form.

The branched chain amino acid can be valine, leucine, and/or isoleucine. In this case, the mixing ratio of isoleucine, leucine, and valine can be generally isoleucine:leucine:valine=1.0:1.5-3.0:0.5-1.5 in a weight ratio. Particularly, the ratio of leucine can be increased to about 1.5- to 3-fold relative to valine.

The nutritional composition can contain B vitamin. Examples of B vitamins include vitamin $B_1$ such as thiamine; vitamin $B_2$ such as riboflavin; vitamin $B_6$ such as pyridoxine, pyridoxal, pyridoxamine; vitamin $B_{12}$ such as cyanocobalamin. These may be used alone or in combinations of two or more. B vitamins play an important role in the metabolism of carbohydrates, protein, and lipid. The amount of B vitamins can be 0.2 mg-20.0 mg for vitamin $B_1$, 0.25 mg-20.0 mg for vitamin $B_2$, 0.3 mg-20.0 mg for vitamin $B_6$, and 0.20 μg-10.0 μg for vitamin $B_{12}$, per 100 kcal of the composition.

In addition, the nutritional composition can also contain antioxidant vitamin and antioxidant mineral. Examples of the antioxidant vitamin include vitamin A such as retinol, retinal, retinoic acid; vitamin C such as ascorbic acid; carotenoid such as β-carotene; vitamin E such as α-tocopherol, and the like. Examples of the antioxidant mineral include zinc, selenium, and the like. These may be used alone, or in combinations of two or more. When fat is utilized as an energy source for muscle protein synthesis, since excess radicals are produced and oxidative stress is caused as a result, an antioxidant can be added for the prevention and/or improvement thereof. To achieve sufficient antioxidant activity, the amount of antioxidant vitamin and antioxidant mineral can be 50 μg retinol equivalents-2500 μg retinol equivalents for vitamin A, 10 mg-700 mg for vitamin C, 1 mg-50 mg based on α-tocopherol for vitamin E, 1 mg-50 mg for zinc, and 1.0 μg-50.0 μg for selenium, per 100 kcal of the composition.

The nutritional composition can also contain vitamins other than B vitamins and antioxidant vitamins (e.g., vitamin D, vitamin K, niacin, folic acid, pantothenic acid, biotin etc.), and minerals other than antioxidant minerals (e.g., sodium, calcium, iron, phosphorus, magnesium, potassium, copper, iodine, manganese, chrome, molybdenum etc.). These may be used alone, or in combinations of two or more.

In addition, the nutritional composition can contain a medium chain fatty acid oil as a lipid source. The "medium chain fatty acid" can mean a fatty acid having 8-10 carbons, such as caprylic acid, capric acid. The term "medium chain fatty acid oil" can also mean fats and oils including triglycerides of the aforementioned medium chain fatty acid, and the like. The medium chain fatty acid can be characterized in that it is digested and absorbed about 4 times more rapidly than long chain fatty acids that are generally present in fats and oils, delivered after absorption in the liver via the portal vein without passing through lymphatic vessels, and rapidly metabolized. Therefore, it can be preferably utilized as an energy source. Fats and oils containing a large amount of medium chain fatty acids such as coconut oil, palm oil, palm kernel oil can be used as the medium chain fatty acid oil. Coconut and palm oils, and the like, can be extracted and purified from natural plants such as coconut. However, a commercially available product can be conveniently used. Medium chain fatty acid oils can be added in an amount of 10 wt %-65 wt % relative to the total weight of lipid.

The nutritional composition can contain, as a fat source other than medium chain fatty acid oil, for example, edible vegetable oil such as cottonseed oil, sunflower oil, peanut oil, canola oil, soybean oil, safflower oil, olive oil, rice oil, corn oil, benne oil, cacao butter, edible animal oil such as beef fat, lard, fish oil, butter, butter oil, and processed fats and oils such as shortening. These may be used alone, or in combinations of two or more.

The nutritional composition can contain, as a carbohydrate source, for example, glucide, dietary fiber, and the like. Examples of glucide include dextrin, oligosaccharide, saccharose, glucose, fructose, starch, and the like. Examples of dietary fiber include water-soluble dietary fiber (e.g., indigestible dextrin, pectin, galactomannan etc.), insoluble dietary fiber (e.g., soybean- and wheat-derived bran, crystalline cellulose etc.), and the like. These may be used alone, or in combination of two or more kinds.

The nutritional composition can contain as a protein source, amino acids, peptides, proteins, and the like. As the protein, animal-derived protein such as casein, acid casein, casein sodium, casein calcium, whey protein, milk serum whey protein, fish protein, egg protein, and hydrolysates thereof, and plant-derived protein such as soybean protein, wheat protein, corn protein, and hydrolysates thereof, and the like can be added. The total amount of these protein sources in the nutritional composition can be 2-20 g per 100 kcal of the composition. When these protein sources contain branched chain amino acids, one should include the amount of the branched chain amino acid from these sources when calculating the total amount of the branched chain amino acids in the composition.

When the nutritional composition contains a branched chain amino acid in a protein form, the total content of the protein source in the nutritional composition also including the protein can be 2-20 g per 100 kcal of the composition. Particularly, when the chosen branched chain amino acid in the nutritional composition consists only of a branched chain amino acid in the free form, the content of the total amount of the protein source in the nutritional composition can be 1.0-15 g per 100 kcal of the composition.

The nutritional composition can be directly administered into the bowels and stomach of patients showing insufficient oral ingestion, by using an administration tube, or when oral ingestion is possible, it can be given as a food or drink. Lysine and n-3 fatty acid, and further, one or more kinds of branched chain amino acids such as valine, leucine and/or isoleucine, and the like, may be directly mixed and ingested as a nutritional composition, or the composition can also be formulated with a pharmaceutically acceptable carrier and provided as a pharmaceutical product. Alternatively, the composition can also be provided in the form of food or drinks, such as food claiming specified health or nutritional benefits, by adding to a food or drink, or a food additive, or can be provided as a general food or drink.

The nutritional composition can be formulated as a liquid preparation such as an elixir, suspension, syrup, emulsion, ampoule; or a solid preparation such as gel, gum, drop, powder, granule, pill, tablet (including sugar-coated tablet, film-coated tablet), capsule, package agent, powder, and the like.

Examples of the pharmaceutically acceptable carrier, which can be used for formulating the nutritional composition, include cellulose and a derivative thereof such as crystalline cellulose, hydroxypropylcellulose; excipients such as natural polymer compound (gum arabic, sodium alginate etc.); binders such as guar gum, stearic acid, polymeric polyvinylpyrrolidone; lubricants such as talc, polyethylene glycol 6000; disintegrants such as adipic acid, surfactants such as sucrose fatty acid ester, soybean lecithin, polyoxyethylene hydrogenated castor oil, polyoxyethylene monostearic acid ester; thickeners such as sodium carboxymethylcellulose, carboxyvinyl polymer, xanthan gum, gelatin; coating agents such as ethyl acrylate-methyl methacrylate copolymer dispersion, caramel, Carnauba wax, shellac-pullulan; pH adjusters such as citric acid, sodium citrate, acetic acid, sodium acetate, sodium hydroxide; antioxidants such as erythorbic acid, butylhydroxyanisole, propyl gallate; flavoring agents such as aspartame, licorice extract, saccharin; preservatives such as sodium benzoate, sodium edetate, sorbic acid, sodium sorbate, methyl paraoxybenzoate, butyl paraoxybenzoate; colorants such as ferric oxide red, yellow iron oxide, black iron oxide, carmine, Food Color blue No. 1, Food Color yellow No. 4, Food Color Red No. 2, and the like.

When the nutritional composition can be provided as food and drink, such products can include liquid products such as drinks, milk products such as milk, milk beverage, yogurt, jelly products such as jelly drinks, jelly, gum products, powder products, granular products, sheet products, capsule products, tablet products, solid products such as snack bar, cookie, and the like.

Examples of materials which can be used for forming the nutritional composition as a food or drinks include a sweetener, colorant, preservative, thickening stabilizer, antioxidant, color former, bleach, fungicide, gum base, bittering agent, enzyme, gloss agent, acidulant, seasoning, emulsifier, enhancement agent, agent for production, flavor, spice, and the like.

When the nutritional composition is provided as food and drink, it can be packaged as a single serving. Single serving packaging can be used when the amount of food and drink to be ingested per meal is determined in advance. Examples thereof include a single serving package such as pack, bag, bottle, box in case of drinks, gum, jelly, yogurt, cookie and the like. The single serving package can be a pack, bag, and the like, in case of foods in the form of granule, powder, slurry, and the like. Particularly, when the food or drink are specified for health, nutritional, special-use, or invalid uses, the composition can be packaged as a single serving unit amount, such as when the composition is to be suspended or dissolved in a bottle to give a drink etc., for a single consumption and the like.

The amount of the nutritional composition to be ingested per day can be individually determined depending on the age, sex, body weight, meal condition, and the like, and can be about 50 kcal-2000 kcal for an adult per day. This amount can be ingested in about 1 to 3 portions a day. When the nutritional composition is formulated in a single serving food or drink in a package form of one ingestion amount unit, the amount to be ingested one time as determined above can be individually packed.

The nutritional composition can be produced by conventional formulation techniques and food production techniques.

The nutritional composition can be useful as a pharmaceutical product, food or drink, and the like for increasing muscle mass and/or suppressing a decrease in muscle mass. In addition, the nutritional composition can be useful as a pharmaceutical product, food or drink, and the like for increasing energy consumption. Furthermore, the nutritional composition can be useful as a pharmaceutical product, food or drink, and the like for the prophylaxis and/or improvement of a decrease in muscle mass unaccompanied by an increase in inflammatory cytokine.

The nutritional composition can be useful as a pharmaceutical product, food and drink, and the like for the prevention and/or improvement of muscle weakness symptom.

The muscle weakness symptom is also called sarcopenia, decreases the amount of activity due to the decreased muscular strength of four limbs, and further causes chronic obstructive pulmonary diseases (COPD). The nutritional composition can effectively prevent and/or improve such muscle weakness symptom.

The nutritional composition can be useful as a pharmaceutical product, food or drink, and the like for enhancing rehabilitation effect for muscle recovery. Recovery of muscular strength by rehabilitation takes time, but the muscle function needs to be recovered before progression of contracture. The composition can increase muscle mass and is useful for enhancing rehabilitation effect. It is also useful for the improvement of low nutrient condition, improvement of deterioration in locomotorium, prophylaxis and/or improvement of locomotive syndrome, prevention of falling and the like, as well as increase of muscle mass in sports and the like.

The nutritional composition can be useful as a pharmaceutical product, food or drink, and the like for decreasing visceral fat. Increase in visceral fat induces insulin resistance, which can result in the development or progression of various diseases associated with insulin resistance. The nutritional composition can effectively reduce visceral fat.

The nutritional composition is useful as a pharmaceutical product, food or drink, and the like for the prophylaxis and/or improvement of dyslipidemia associated with visceral fat increase. When the visceral fat increases, dyslipidemia such as high LDL-cholesterolemia, hypertriglyceridemia, remnant hyperlipoproteinemia, high small dense LDL, and low HDL-cholesterolemia can occur. As a result of the onset of dyslipidemia, the production of lipoperoxides such as LDL cholesterol peroxide increases, and the risk of developing atherosclerosis becomes high. The nutritional composition can effectively suppress the onset of dyslipidemia such as increased blood LDL cholesterol associated with visceral fat increase, and is useful for the prevention and/or improvement of dyslipidemia associated with visceral fat increase.

The nutritional composition is useful as a pharmaceutical product, food or drink, and the like for the prophylaxis and/or improvement of hyperglycemia associated with visceral fat increase. Insulin resistance due to visceral fat increase depresses glucose uptake efficiency from blood into the cell, and causes hyperglycemia. The nutritional composition is useful for the prophylaxis and/or improvement of hyperglycemia associated with visceral fat increase.

The nutritional composition is useful as a pharmaceutical product, food or drink, and the like for the prophylaxis and/or improvement of fatty liver and deterioration of liver function associated with visceral fat increase. Mesenteric fat, which is representative of increased visceral fat, releases free fatty acids into the portal blood, and causes accumulation of fat in the liver, which is the nearest organ. On the other hand, hyperinsulinemia due to insulin resistance also activates synthesis of fat from sugar in the liver. Furthermore, fat accumulation in the liver aggravates liver function. The nutritional composition is useful for the prophylaxis and/or improvement of fatty liver and deterioration of liver function associated with visceral fat increase.

The nutritional composition can be useful as a pharmaceutical product, food or drink, and the like for the prophylaxis and/or improvement of a a decrease in basal energy consumption. A decrease in the basal energy consumption in elderly people means depressed energy utilization in the body, which exerts a vast influence on the metabolism such as synthesis of proteins to be utilized as energy. In addition, when the energy utilization is depressed, the ingested energy becomes redundant, and the redundant energy accumulates as fat. The nutritional composition can be useful for the prophylaxis and/or improvement of a decrease in the basal energy consumption.

The nutritional composition can be useful as a pharmaceutical product, food or drink, and the like for the prophylaxis and/or improvement of a decrease in basal body temperature. When the body temperature is low, the metabolic activity becomes weak, and energy production and body protein synthesis are depressed. Particularly, in elderly people since thermoregulatory competence is also attenuated, a low body temperature cannot be easily increased. The nutritional composition is useful for the prophylaxis and/or improvement of a decrease in the basal body temperature.

The nutritional composition can be a multipurpose type comprehensive nutritional composition containing lysine and n-3 fatty acid, and further, one or more kinds of branched chain amino acids such as valine, leucine and/or isoleucine, in a powder form and the like.

The nutritional composition can be used for increasing muscle mass and/or suppressing a further decrease in muscle mass of a person with a decreased muscle mass (e.g., elderly people, bedridden person etc.). It is particularly effective when visceral fat associated with dyslipidemia, hyperglycemia, fatty liver, and/or deterioration of liver function is particularly used as an energy source for muscle protein synthesis. The nutritional composition greatly contributes to those people having no effective nutritional composition heretofore.

EXAMPLES

The present invention is now explained based on the following non-limiting Examples.

[Example 1] Preparation of Nutritional Composition

The nutritional composition shown in Table 1 was prepared with the goal of providing an optimum nutritional effect for elderly people. The amounts of the starting materials of the liquid are shown in Table 2. Each component and an emulsifier were added to water, mixed, and an emulsion step was repeatedly performed in a high-pressure emulsifying machine under pressurization of 500-1,000 kg/cm$^2$ to give an emulsion composition. As the amino acid composition, L-leucine (0.38 g), L-valine (0.19 g), L-isoleucine (0.23 g) and L-lysine (0.32 g) were added per 100 kcal of the composition. In this case, the total amount of the branched chain amino acids (leucine, valine, isoleucine) including those derived from a protein was 1.46 g per 100 kcal of the composition. The emulsion composition was placed in an aluminum bag by a conventional filling machine, and sterilized by a retort sterilization machine under general conditions. The nutritional composition of this Example stably contained all ingredients one year later, and the viscosity at 25° C. was 9 mPa·s. A thickener was added to the regulated liquid, whereby a nutritional composition with regulated thickness (1,000-7,000 mPa·s) or jelly could be produced. Furthermore, even when the amount of the amino acid added was 2-fold, similar production was possible. The calorie density of the nutritional composition was 1.0 kcal/ml.

TABLE 1

Example 1 nutritional composition

| component | unit | content/100 kcal |
|---|---|---|
| Protein source | g | 4.5 |
| L-leucine | g | 0.38 |
| L-valine | g | 0.19 |
| L-isoleucine | g | 0.23 |
| L-lysine | g | 0.32 |
| lipid | g | 2.80 |
| medium chain fatty acid | g | 0.54 |
| containing EPA | mg | 67 |
| containing n-3 fatty acid | g | 0.195 |
| hydrocarbonate | g | 14.2 |
| carbohydrates | g | 13 |
| dietary fiber | g | 1.2 |
| sodium | mg | 185 |
| calcium | mg | 65 |
| iron | mg | 0.8 |
| phosphorus | mg | 55 |
| magnesium | mg | 26 |
| potassium | mg | 130 |
| copper | mg | 0.11 |
| iodine | µg | 13 |
| manganese | mg | 0.34 |
| selenium | µg | 2.5 |
| zinc | mg | 1.65 |
| chrome | µg | 2.5 |
| molybdenum | µg | 2.1 |
| vitamin A | µg RE *1 | 81 |
| vitamin D | µg | 0.46 |
| vitamin E | mg α-TE *2 | 2.73 |
| vitamin K | µg | 6.3 |
| vitamin $B_1$ | mg | 0.6 |
| vitamin $B_2$ | mg | 0.36 |
| niacin | mg NE *3 | 1.3 |
| vitamin $B_6$ | mg | 0.6 |
| folic acid | µg | 20 |
| vitamin $B_{12}$ | µg | 0.5 |
| biotin | µg | 4.2 |
| pantothenic acid | mg | 0.5 |
| vitamin C | mg | 40.0 |

*1 retinol equivalents
*2 amount based on α-tocopherol
*3 niacin equivalents

TABLE 2

Example 1 starting material composition
○ Example 1 composition

| starting material | mixing ratio (w/v %) | amount added | unit |
|---|---|---|---|
| casein sodium | 3.8000 | 114 | kg |
| Lysine hydrochloride | 0.4000 | 12.0 | kg |
| leucine | 0.3833 | 11.5 | kg |
| isoleucine | 0.2300 | 6.90 | kg |
| valine | 0.1900 | 5.70 | kg |
| dextrin | 11.07 | 332 | kg |
| sugar | 2.367 | 71.0 | kg |
| edible vegetable oil | 1.387 | 41.6 | kg |
| medium-chain triglyceride | 0.5367 | 16.1 | kg |
| fish oil | 0.2633 | 7.90 | kg |
| citric acid | 0.1593 | 4.78 | kg |
| trisodium citrate | 0.5433 | 16.3 | kg |
| potassium carbonate | 0.2280 | 6.84 | kg |
| magnesium chloride | 0.2207 | 6.62 | kg |
| calcium lactate | 0.2960 | 8.88 | kg |
| glycerolcalcium phosphate | 0.1303 | 3.91 | kg |
| mineral yeast premix *1 | 0.06293 | 1.888 | kg |
| Indigestible dextrin | 1.5070 | 45.2 | kg |
| emulsifier | 0.6606 | 19.8 | kg |
| β-carotene oil | 0.0015 | 45.0 | g |
| vitamin E | 0.0052 | 156 | g |
| vitamin premix *2 | 0.1035 | 3.105 | kg |
| sodium ascorbate | 0.0810 | 2.43 | kg |
| prepared water | 83.08 | 2492 | kg |
| total | 107.7 | 3231 | kg |

*1 mineral yeast premix composition

| starting material | amount | unit |
|---|---|---|
| molybdenum-containing yeast | 13.0 | g |
| water-soluble chrome-containing yeast | 21.0 | g |
| selenium-containing yeast | 37.0 | g |
| manganese-containing yeast | 203 | g |
| copper-containing yeast | 337 | g |
| zinc-containing yeast | 707 | g |
| biotin-containing yeast | 344 | g |
| sodium ferrous citrate | 226 | g |
| total | 1.888 | kg |

*2 vitamin premix composition

| starting material | amount | unit |
|---|---|---|
| folic acid | 0.60 | g |
| vitamin D powder | 8.50 | g |
| vitamin B 12 0.1% powder | 15.0 | g |
| riboflavin 5'-phosphate sodium | 19.1 | g |
| calcium pantothenate | 22.3 | g |
| pyridoxine hydrochloride | 28.6 | g |
| nicotinic acid amide | 38.5 | g |
| thiamine hydrochloride | 40.7 | g |
| vitamin A powder | 45.7 | g |
| vitamin K2 powder | 58.0 | g |
| kelp extract powder | 278 | g |
| sodium erythorbate | 2550 | g |
| total | 3.105 | kg |

[Example 2] Preparation of Integrated Nutritional Composition

In the same manner as in Example 1, the nutritional composition shown in Table 3 was prepared. In the same manner as in Example 1, each component and an emulsifier were added to water, mixed, and an emulsion step was repeatedly performed several times in a high-pressure emulsifying machine under pressurization of 50-500 kg/cm² to give an emulsion composition. As the amino acid composition, L-leucine (0.28 g), L-valine (0.14 g), L-isoleucine (0.14 g) and L-lysine (0.28 g) were added per 100 kcal of the composition. In this case, the total amount of the branched chain amino acids (leucine, valine, isoleucine) including those derived from a protein is 1.30 g per 100 kcal of the composition. The emulsion composition was placed in an aluminum bag by a conventional filling machine, and sterilized by a retort sterilization machine under general conditions. The nutritional composition of this Example stably contained all ingredients one year later, and the viscosity at 25° C. was 4,000 mPa·s. An appropriate amount of a thickener was added to the regulated liquid to further impart viscosity, whereby a nutritional composition with regulated thickness (1,000-7,000 mPa·s) or jelly could be produced. The calorie density of the nutritional composition was 2.0 kcal/ml.

TABLE 3

Example 2 nutritional composition

| component | unit | content/100 kcal |
|---|---|---|
| Protein source | g | 4.5 |
| L-leucine | g | 0.28 |
| L-valine | g | 0.14 |
| L-isoleucine | g | 0.14 |
| L-lysine | g | 0.28 |
| lipid | g | 2.80 |
| medium chain fatty acid | g | 0.60 |
| containing EPA | mg | 67 |
| containing n-3 fatty acid | g | 0.19 |
| hydrocarbonate | g | 14.2 |
| carbohydrates | g | 13 |
| dietary fiber | g | 1.2 |
| sodium | mg | 185 |
| calcium | mg | 65 |
| iron | mg | 0.8 |
| phosphorus | mg | 55 |
| magnesium | mg | 26 |
| potassium | mg | 130 |
| copper | mg | 0.11 |
| iodine | µg | 13 |
| manganese | mg | 0.34 |
| selenium | µg | 2.5 |
| zinc | mg | 1.65 |
| chrome | µg | 2.5 |
| molybdenum | µg | 2.1 |
| vitamin A | µg RE *1 | 81 |
| vitamin D | µg | 0.46 |
| vitamin E | mg α-TE *2 | 2.73 |
| vitamin K | µg | 6.3 |
| vitamin B$_1$ | mg | 0.6 |
| vitamin B$_2$ | mg | 0.36 |
| niacin | mg NE *3 | 1.3 |
| vitamin B$_6$ | mg | 0.6 |
| folic acid | µg | 20 |
| vitamin B$_{12}$ | µg | 0.5 |
| biotin | µg | 4.2 |
| pantothenic acid | mg | 0.5 |
| vitamin C | mg | 40.0 |

*1 retinol equivalents
*2 amount based on α-tocopherol
*3 niacin equivalents

[Example 3] Preparation of Powder Nutritional Composition

The powder type nutritional composition shown in Table 4 was prepared. The amounts of the starting materials of the liquid are shown in Table 5. Each component and an emulsifier were added to an appropriate amount of water, mixed, and an emulsion step was repeatedly performed several times in a high-pressure emulsifying machine under pressurization of 2-50 kg/cm$^2$ to give an emulsion composition. This emulsion composition was spray dried to give a powder nutritional composition. As the amino acid composition, L-leucine (3.9 g), L-valine (2.4 g), L-isoleucine (2.0 g) and L-lysine (4.1 g) were added per 100 kcal of the composition. This powder nutritional composition was placed in an aluminum bag by a conventional filling machine. The powder nutritional composition of this Example stably contained all ingredients one year later. This nutritional composition could be used even after dissolving in warm water and mixing with a nutritional supplement.

TABLE 4

Example 3 nutritional composition

| component | unit | content/100 kcal |
|---|---|---|
| Protein source | g | 12.4 |
| L-leucine | g | 3.9 |
| L-valine | g | 2.4 |
| L-isoleucine | g | 2.0 |
| L-lysine | g | 4.1 |
| lipid | g | 4.8 |
| containing EPA | mg | 812 |
| containing n-3 fatty acid | g | 1.34 |
| hydrocarbonate | g | 1.6 |
| vitamin A | µg RE *1 | 413 |
| vitamin E | mg α-TE *2 | 19.2 |
| vitamin B$_1$ | mg | 5.3 |
| vitamin B$_2$ | mg | 3.2 |
| vitamin B$_6$ | mg | 5.1 |
| vitamin C | mg | 392.9 |

*1 retinol equivalents
*2 amount based on α-tocopherol

TABLE 5

Example 3 starting material composition

| name of starting materials | mixing ratio w/v % |
|---|---|
| L-leucine | 18.65 |
| L-isoleucine | 11.30 |
| L-valine | 9.475 |
| L-lysine hydrochloride | 24.64 |
| fish oil | 22.99 |
| vitamin A oil 500,000 IU/g | 0.01230 |
| thiamine hydrochloride | 0.02571 |
| riboflavin 5'-phosphate sodium | 0.02037 |
| Pyridoxine hydrochloride | 0.03038 |
| tocopherol 40% | 0.2146 |
| L ascorbic acid Na | 2.146 |
| emulsifier | 10.487 |
| | 100.0 |

[Experimental Example 1] Study of Enrichment Effect of Amino Acid and n-3 Fatty Acid in Visceral Fat Increase Animal Model The effects of amino acid and n-3 fatty acid in the nutritional composition to improve visceral fat increase and muscle mass decrease was examined by the following experiment. To be specific, 10-week-old male C57BL/6J mice were fed with the same high-fat diet as in 1B group shown in Table 6 to prepare visceral fat increase models. They were divided into 3 groups (each group N=5-9), and fed an experimental diet of the composition shown in Table 6 for 2 weeks. 1B group was continuously fed a high-fat diet containing a large amount of beef fat rich in saturated fatty acid. 1C group was fed an experimental diet of a standard composition. 1D group was fed an experimental diet with an enriched composition, wherein the total amount of protein and fat was not changed, and 0.32 g, 0.8 g, 0.24 g of lysine, BCAA (3 kinds of branched chain amino acid consisting of leucine, valine, isoleucine) and fish oil, respectively, per 100 kcal of experimental diet, were used for substitution. In this case, 1D group was fed with 1.46 g of the total amount of BCAA including those derived from protein, 0.24 g of the total amount of n-3 fatty acid and 67 mg of eicosapentaenoic acid (EPA), each per 100 kcal of the experimental diet. 1A group as a normal control group was fed an experimental diet with a standard composition throughout the test period, without a high-fat diet. Two weeks after ingestion of experimental diets, they were fasted for 16 hr, and the mesenteric fat weight and gastrocnemius muscle weight were measured. The results are shown in FIG. 1.

and n-3 fatty acid were tested either singly or in combination. That is, visceral fat increase models were prepared in the same manner as in Experimental Example 1, divided into 4 groups (each group N=5-9), and fed an experimental diet of the composition shown in Table 7 for 2 weeks. The 2A

TABLE 6 experimental diet composition table (content per 100 kcal of experimental diet)

| group constitution | Protein source (g) | | | | | fat (g) | | | | hydro-carbonate (g) |
| --- | --- | --- | --- | --- | --- | --- | --- | --- | --- | --- |
| | casein (g) | L-lysine (g) | L-valine (g) | L-leucine (g) | L-isoleucine (g) | soybean oil (g) | beef fat (g) | fish oil (g) containing EPA (mg) | n-3 fatty acid amount contained (g) | |
| 1A group | 4.5 | | | | | 2.80 | | | 0.17 | 15.4 |
| 1B group | 4.5 | | | | | 0.56 | 5.17 | | 0.05 | 7.2 |
| 1C group | 4.5 | | | | | 2.80 | | | 0.17 | 15.4 |
| 1D group | 3.38 | 0.32 | 0.2 | 0.4 | 0.2 | 2.56 | | 0.2467 | 0.24 | 15.4 |

The body weight of the 1B group fed a high-fat diet was 1.2 times that of the 1A group fed a general diet. Thereafter, throughout the evaluation period when the experimental diet was given, the body weight of the 1D group was lower than that of the 1C group, even though the calorie intake was the same (1D: 31.7±3.3 g, 1C: 34.4±1.7 g). Moreover, as shown in FIG. 1, the mesenteric fat weight significantly increased in the 1B group as compared to the 1A group, and the gastrocnemius muscle weight was significantly decreased in the 1B group as compared to the 1A group. On the other hand, the mesenteric fat weight was significantly decreased in the 1D group and the gastrocnemius muscle weight was significantly increased, as compared to the 1C group. In this high-fat diet ingestion model, CRP in plasma (C reactive protein) showed no difference between groups (1A group: 7.7±2.4 ng/ml, 1B group: 9.0±3.3 ng/ml, 1C group: 7.0±5.3 ng/ml, 1D group: 8.6±3.9 ng/ml).

From these test results, a diet enriched with lysine, BCAA, eicosapentaenoic acid can decrease mesenteric fat weight, which is the weight of visceral fat, and increase gastrocnemius muscle weight.

Figures 2A, 2B:
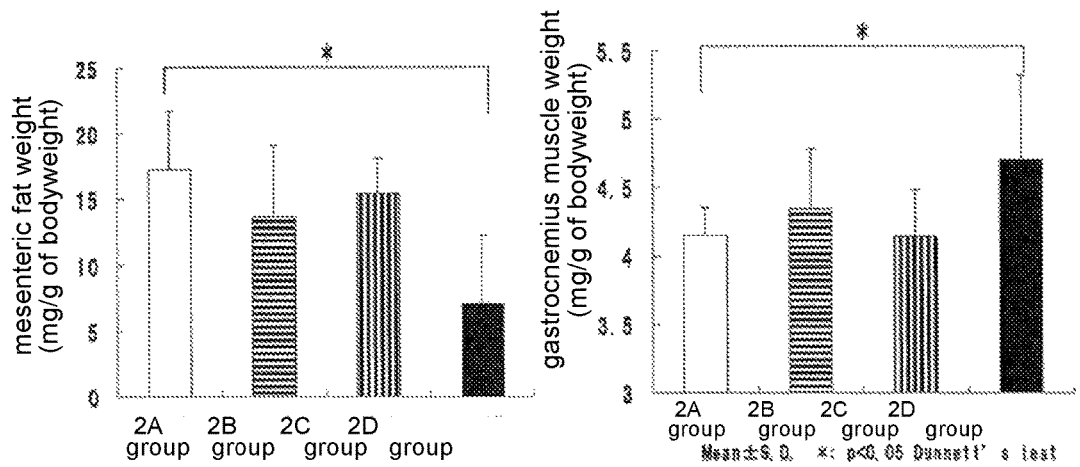
FIGS. 2A and 2B shows mesenteric fat weight and gastrocnemius muscle weight respectively, of the groups of as outlined in Experimental Example 2.
Figure 3A:
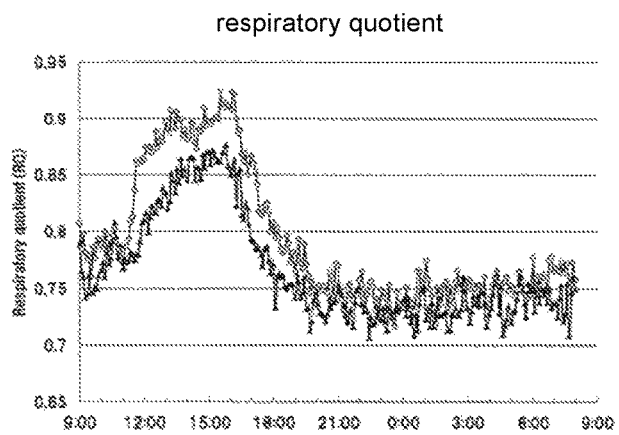
FIGS. 3A, 3B, 3C, and 3D shows respiratory quotient (FIGS. 3A and 3B) and energy consumption (FIGS. 3C and 3D) of the groups as outlined in Experimental Example 3.
Figure 3B:
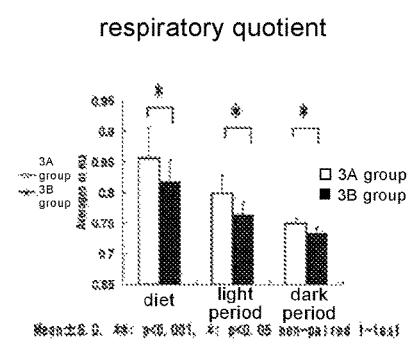
Figure 3C:
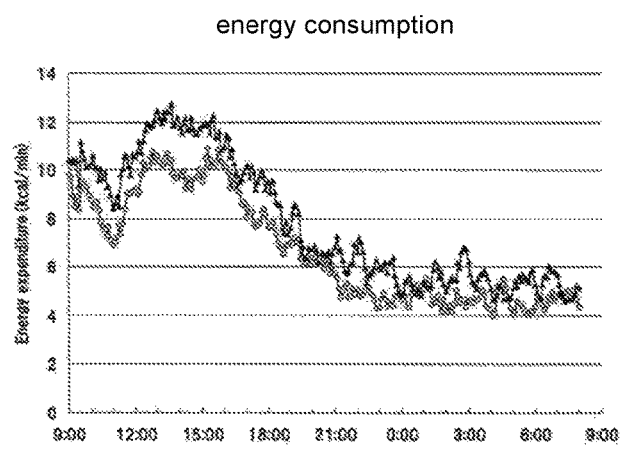
Figure 3D:
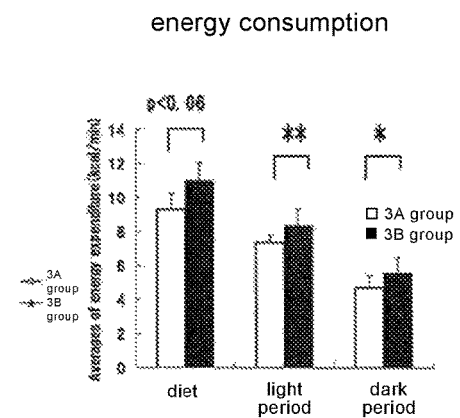

[Experimental Example 2] Single Effect and Combined Effect of Amino Acids (Lysine, BCAA) and n-3 Fatty Acid As a result of Experimental Example 1, enrichment with amino acid and n-3 fatty acid was shown to be necessary for decreasing mesenteric fat weight and increasing gastrocnemius muscle weight. However, it is not clear whether each component shows this effect alone. Therefore, amino acid group was fed an experimental diet of a standard composition. The 2D group was fed with an experimental diet an enriched composition, wherein the total amount of protein and fat was not changed, and 0.32 g, 0.8 g, 0.24 g of lysine, BCAA and fish oil, respectively, per 100 kcal of experimental diet, were used. In this case, the 2D group was fed 1.46 g of the total amount of BCAA including those derived from protein, 0.24 g of the total amount of n-3 fatty acid, and 67 mg of eicosapentaenoic acid (EPA), each per 100 kcal of the experimental diet. Furthermore, the 2B group and 2C group were fed an experimental diet enriched with amino acid or n-3 fatty acid. Two weeks after ingestion of the experimental diet, they were fasted for 16 hr, and the mesenteric fat weight and gastrocnemius muscle weight were measured. The results are shown in FIG. 2.

TABLE 7 experimental diet composition table (content per 100 kcal of experimental diet)

| | Protein source (g) | | | | | fat (g) | | | hydro-carbonate (g) |
| --- | --- | --- | --- | --- | --- | --- | --- | --- | --- |
| | casein (g) | L-lys (g) | L-val (g) | L-leu (g) | L-ile (g) | soybean oil (g) | fish oil (g) with EPA (mg) | n3 fatty acid amount (g) | |
| 2A | 4.5 | | | | | 2.80 | | 0.17 | 15.4 |
| 2B | 3.38 | 0.32 | 0.2 | 0.4 | 0.2 | 2.80 | | 0.17 | 15.4 |
| 2C | 4.5 | | | | | 2.56 | 0.2467 | 0.24 | 15.4 |
| 2D | 3.38 | 0.32 | 0.2 | 0.4 | 0.2 | 2.56 | 0.2467 | 0.24 | 15.4 |

The total calorie intake was not different between groups during ingestion of the experimental diet. As shown in FIG. 2, the 2D group significantly decreased mesenteric fat weight, which is the visceral fat, and significantly increased gastrocnemius muscle weight. In contrast, decrease of mesenteric fat weight and increase of gastrocnemius muscle weight in the 2B group and the 2C group were clearly weak as compared to the effects in the 2D group, and the effect in the 2B group even combined with the effect in the 2C group was still lower than the effect in the 2D group.

From these results, the mesenteric fat decreasing action and gastrocnemius muscle increasing action by the enriched diet was not provided by the amino acid nor the n-3 fatty acid alone, but by a synergistic effect of the amino acid and n-3 fatty acid in combination. That is, in this test, the combined use of lysine and n-3 fatty acid, and further, branched chain amino acid was shown to be useful.

[Experimental Example 3] Energy Metabolism Enhancing Effect and Mitochondria Increasing Effect of Amino Acids and n-3 Fatty Acid Then, the influence of the nutritional composition enriched with amino acid and n-3 fatty acid on energy metabolism using an exhaled gas metabolism measuring apparatus was examined. That is, visceral fat increase model prepared in the same manner as in Experimental Example 1 was fed an experimental diet with a standard composition (3A group) or an experimental diet with an enriched composition (3B group) shown in Table 8, and subjected to an evaluation. To stabilize the amount of intake, a one-week experimental diet acclimation period was set, after which one animal was placed in each cage within 2 weeks, and oxygen consumption (ml/min) and carbon dioxide production (ml/min) were measured (metabolism measuring system for small animals MK-5000 RQ, Muromachi Kikai Co., Ltd.). During the measurement, an experimental diet was given, and the amount of intake was measured. The respiratory quotient was calculated by carbon dioxide production÷oxygen consumption, and the energy consumption was calculated by the formula of Weir [energy consumption (kcal/min)=3.9 (kcal)×oxygen consumption (ml/min)+1.1 (kcal)×carbon dioxide production (ml/min)]. The results are shown in FIG. 3.

and, on the last day of the test, the liver and gastrocnemius muscle were rapidly collected and cryopreserved. DNA was extracted from each of the cryopreserved liver (100 mg) and gastrocnemius muscle (200 mg) by using ISOGEN (Japan gene). To 50 ng DNA were added the primer of d-loop of mitochondria shown in Table 9 and SYBER GREEN Master Mix (ABI), and amplification and quantification analysis were performed using an ABI 7700 detector. For the amendment of DNA amount, gene cyclophillin A (intron code part) on the chromosome was used. As for the synthesized primer, the occurrence of desired production was confirmed by agarose electrophoresis after PCR reaction.

TABLE 9

| DNA primer of mitochondria and chromosome | | |
|---|---|---|
| Gene | sense | antisense |
| ch cyclophillin A | ACACGCCATAATGGCACTGG (Sequence Listing SEQ ID NO: 1) | CAGTCTTGGCAGTGCAGAT (Sequence Listing SEQ ID NO: 2) |
| mt d-loop | CGCAAAACCCAATCACCTAA (Sequence Listing SEQ ID NO: 3) | TTGGGGTTTGGCATTAAGAG (Sequence Listing SEQ ID NO: 4) |

Since mitochondria plays an important role in fat combustion in the cell, the number of intracellular mitochondria was analyzed. While only one intranuclear chromosomal DNA is present in the cell, the number of mitochondria is not the same. Therefore, the amount of mitochondria in the cell was assumed by a method of determining the ratio of the DNA amount of mitochondrial coding gene and that of the nuclear coding gene. The results are shown in FIG. 4.

As shown in FIG. 4, the mitochondrial DNA amount of the 3B group significantly increased in both the liver and gastrocnemius muscle, as compared to the 3A group.

By this test, a nutritional composition containing lysine and n-3 fatty acid, and further, a branched chain amino acid,

TABLE 8

| experimental diet composition table (content per 100 kcal of experimental diet) | | | | | | | | | |
|---|---|---|---|---|---|---|---|---|---|
| | Protein source (g) | | | | | fat (g) | | | |
| | casein (g) | L-lys (g) | L-val (g) | L-leu (g) | L-ile (g) | soybean oil (g) | fish oil (g) with EPA (mg) | n3 fatty acid amount (g) | hydro-carbonate (g) |
| 3A | 4.5 | | | | | 2.80 | | 0.17 | 15.4 |
| 3B | 3.38 | 0.32 | 0.2 | 0.4 | 0.2 | 2.56 | 0.2467 | 0.24 | 15.4 |

As shown in FIG. 3, the respiratory quotient of the 3B group decreased significantly as compared to the 3A group during the diet ingestion period (9:00-16:00; diet) and the dark period after eating (16:00-19:00; dark period), and also decreased significantly as compared to the 3A group even in the light period (19:00-9:00: light period), which is free of a direct influence of eating. The energy consumption of the 3B group increases significantly or increases as compared to the 3A group at any period.

In addition, the ability of the nutritional composition to effect the mitochondria was examined. That is, visceral fat increase model prepared in the same manner as in Experimental Example 1 was fed an experimental diet with a standard composition (3A group) or an experimental diet with an enriched composition (3B group) shown in Table 8, can result in an increase in the number of mitochondria to enhance fat utilization, and can increase energy consumption that leads to an increase in the body temperature, and the like.

INDUSTRIAL APPLICABILITY

The nutritional composition as described herein is effective for increasing muscle mass and/or suppressing a decrease in muscle mass. In addition, the nutritional composition is effective for increasing energy consumption. In addition, the nutritional composition is particularly useful for decreasing visceral fat by increasing energy consumption by enhanced fat utilization and the like. In addition, it is useful for the prophylaxis and/or improvement of dyslipidemia, hyperglycemia, fatty liver, and deterioration of liver function associated with visceral fat increase. Furthermore, by increasing muscle mass or suppressing a decrease in muscle mass by fat energy supply and the like, the nutritional composition is also useful for the prophylaxis and/or improvement of sarcopenia, chronic obstructive pulmonary disease (COPD), promotion of rehabilitation effect for muscle recovery, improvement of low nutrient condition, improvement of deterioration in locomotorium, prophylaxis and/or improvement of locomotive syndrome, prevention of falling, increasing muscle mass in sports and the like. Moreover, the nutritional composition is effective for the prophylaxis and/or improvement of a decrease in basal energy consumption, and prophylaxis and/or improvement of a decrease in basal body temperature. Furthermore, the nutritional composition is highly safe, and can be used for a long time without placing an excessive protein load even for elderly people with attenuated kidney function.

While the invention has been described in detail with reference to preferred embodiments thereof, it will be apparent to one skilled in the art that various changes can be made, and equivalents employed, without departing from the scope of the invention. Each of the aforementioned documents is incorporated by references herein in its entirety.

The invention claimed is:

1. A method for decreasing visceral fat or increasing energy consumption, comprising administering to a subject in need thereof an effective amount of a composition comprising:
   i) n-3 fatty acid, and
   ii) an ingredient selected from the group consisting of free lysine, dipeptides containing lysine and lysine salts, and combinations thereof;
   wherein the ingredient is present in the composition in an amount of 0.1 g-10.0 g per 100 kcal of the composition, and
   wherein the n-3 fatty acid is present in the composition in an amount of 0.17 g-5.00 g per 100 kcal of the composition.

2. The method according to claim 1, wherein the subject has increased visceral fat or decreased energy consumption.

* * * * *